United States Patent [19]
Palmer

[11] Patent Number: 5,419,339
[45] Date of Patent: May 30, 1995

[54] FLEXIBLE MICROSURGICAL INSTRUMENT HAVING GROUND DISTAL COIL PORTION

[75] Inventor: Matthew A. Palmer, Miami, Fla.

[73] Assignee: Symbiosis Corporation, Miami, Fla.

[21] Appl. No.: 180,649

[22] Filed: Jan. 13, 1994

Related U.S. Application Data

[63] Continuation-in-part of Ser. No. 62,891, May 17, 1993, which is a continuation-in-part of Ser. No. 865,913, Apr. 9, 1992, Pat. No. 5,228,451.

[51] Int. Cl.$^6$ ............................................. A61B 17/28
[52] U.S. Cl. ...................................... 128/751; 606/205
[58] Field of Search ................. 128/751, 752; 606/113, 606/127, 170, 205, 206, 174, 167, 51, 52

[56] References Cited

U.S. PATENT DOCUMENTS

| | | | |
|---|---|---|---|
| 2,113,246 | 4/1938 | Wappler | 128/321 |
| 4,178,810 | 12/1979 | Takahashi | 74/501 R |
| 4,669,172 | 6/1987 | Petruzzi | 29/456 |
| 4,721,116 | 1/1988 | Schintgen | 128/751 |
| 4,763,668 | 8/1988 | Macek et al. | 128/751 |
| 4,817,630 | 4/1989 | Schintgen et al. | 128/751 |
| 4,936,312 | 6/1990 | Tsukagoshi | 128/749 |
| 4,944,093 | 7/1990 | Falk | 606/205 X |
| 4,982,727 | 1/1991 | Sato | 128/4 |
| 5,035,248 | 7/1991 | Zinnecker | 128/751 |
| 5,094,247 | 3/1992 | Hernandez et al. | 128/751 |
| 5,100,430 | 3/1992 | Avellanet et al. | 606/205 |
| 5,133,727 | 7/1992 | Bales et al. | 128/751 X |
| 5,228,451 | 7/1993 | Bales | 128/751 |
| 5,238,002 | 8/1993 | Devlin | 128/751 |
| 5,241,968 | 9/1993 | Slater | 128/751 |
| 5,242,461 | 9/1993 | Kortenbach et al. | 606/170 X |
| 5,250,073 | 10/1993 | Cottone, Jr. | 606/206 |

FOREIGN PATENT DOCUMENTS

| | | | |
|---|---|---|---|
| 233302 | 2/1986 | Germany | 128/751 |
| 3714560 | 11/1987 | Germany | 606/127 |

*Primary Examiner*—Michael H. Thaler
*Attorney, Agent, or Firm*—David P. Gordon

[57] ABSTRACT

A flexible microsurgical instrument having a distal portion which is ground to a reduced diameter and covered with a stiffening sleeve is disclosed. The instrument includes a proximal actuating handle coupled to a flexible coil containing at least one control wire and a distal end effector coupled to the distal end of the coil and the control wire. A distal portion of the coil is ground to a reduced outer diameter and thus a reduced thickness. The stiffness of the distal portion is enhanced by placing a stiffening sleeve over the ground distal portion. The stiffening sleeve has a thickness substantially equal to one half the difference between the reduced diameter of the ground distal portion and the diameter of the remainder of the coil so that the outer diameter of the coil is substantially constant along its length when the stiffening sleeve is in place.

14 Claims, 1 Drawing Sheet

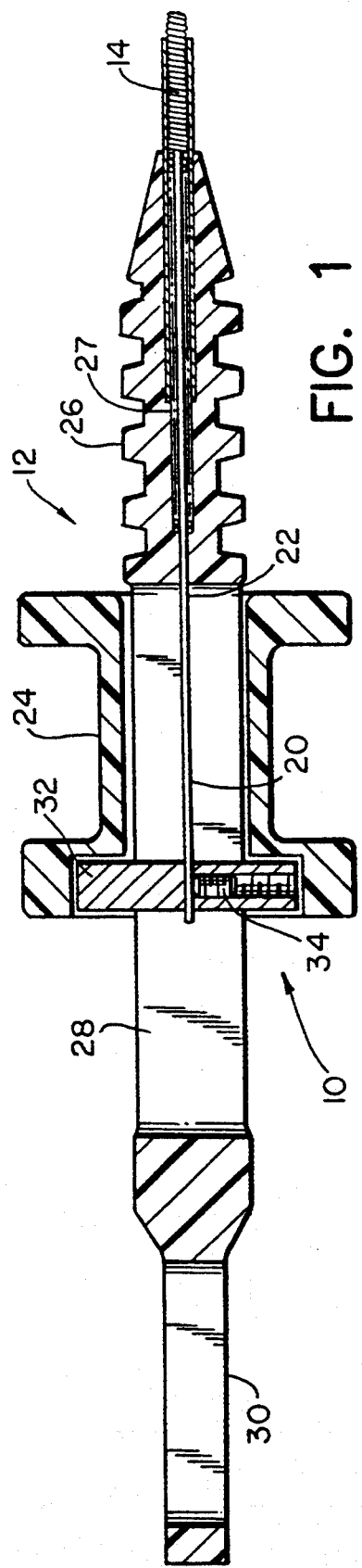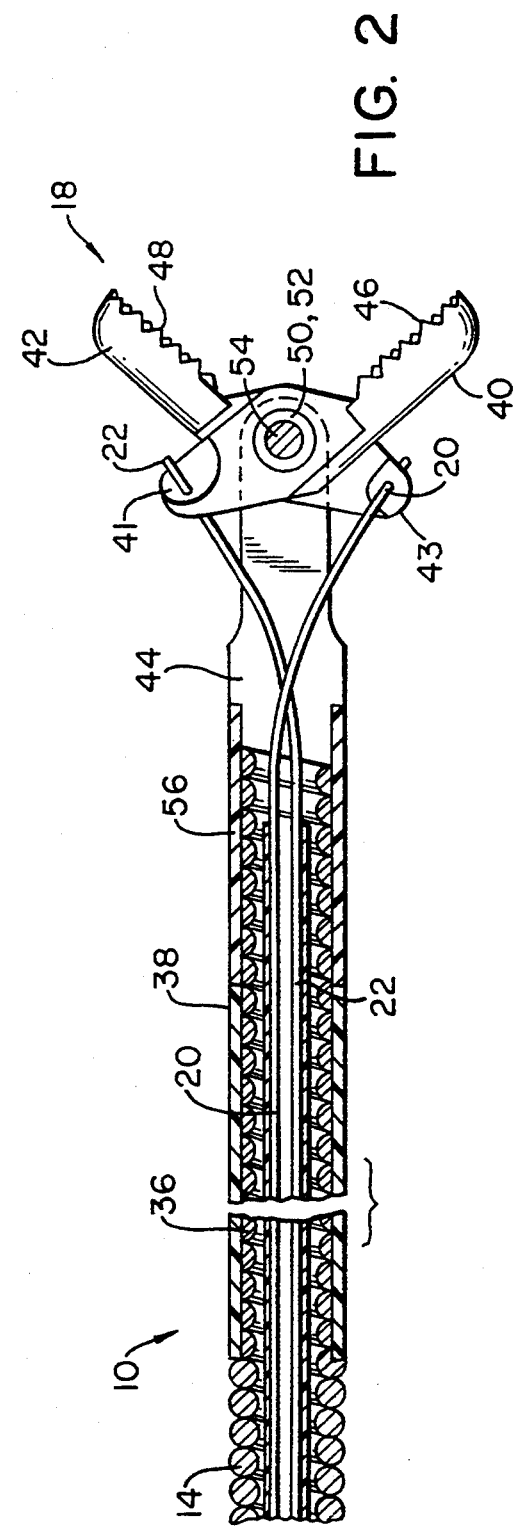

FLEXIBLE MICROSURGICAL INSTRUMENT HAVING GROUND DISTAL COIL PORTION

This application is a continuation-in-part of co-assigned Ser. No. 08/062,891, filed May 17, 1993, which is hereby incorporated herein by reference in its entirety, which is itself a continuation-in-part of Ser. No. 07/865,913, filed Apr. 9, 1992, now issued as U.S. Pat. No. 5,228,451. This application also relates to U.S. Ser. No. 07/837,046 which is hereby incorporated herein by reference in its entirety, which is itself a continuation of Ser. No. 07/521,766 which is now issued as U.S. Pat. No. 5,133,727.

BACKGROUND OF THE INVENTION

1. Field of the Invention

The present invention relates to flexible microsurgical instruments. In particular the present invention relates to flexible microsurgical instruments having a distal portion which is ground to a reduced diameter and fitted with a stiffening sleeve.

2. State of the Art

Flexible microsurgical instruments, in particular endoscopic biopsy forceps, are used for taking tissue samples from the human body for analysis. These instruments typically have a long flexible coil containing one or more control wires coupled to a proximal actuating handle. The actuating handle moves the control wires relative to the coil to effect a tissue sampling operation at the distal end of the coil. A pair of forceps jaws are mounted on a clevis at the distal end of the coil. The forceps jaws are coupled to the control wires so that movement of the control wires causes the jaws to open and close to bite a tissue sample.

The endoscopic biopsy procedure is accomplished through an endoscope which is inserted into a body and guided by manipulation to the biopsy site. The endoscope typically includes a long narrow flexible tube with an optical lens and a narrow lumen for receiving a biopsy forceps. The practitioner guides the endoscope to the biopsy site while looking through the optical lens and inserts the biopsy forceps through the lumen of the endoscope to the biopsy site. While viewing the biopsy site through the optical lens of the endoscope, the practitioner manipulates the actuating handle to effect a tissue sampling operation at the distal end of the instrument. The practitioner must align the open jaws with the tissue to be sampled so that upon closing the jaws, a portion of the tissue is trapped between the jaws. It is a known problem with biopsy forceps that as the jaws are closed the distal end of the flexible coil deflects because the force applied at the actuating handle to the control wires is transferred to the distal end of the flexible coil. The deflection of the distal end of the coil just as the jaws are about to close on a tissue to be sampled often displaces the jaws relative to the tissue to be sampled and results in a failure to acquire the sample or the acquisition of an undesired sample. Therefore it is desirable to stiffen the distal portion of the coil to prevent it from deflecting when the jaws are being closed.

Grandparent U.S. Pat. No. 5,228,451 to Bales et al. discloses a biopsy forceps device having a stiff distal portion. The distal portion of the flexible coil is made stiff by wrapping it with a stiffening sleeve which extends for several inches along the coil and covers a portion of the clevis. The sleeve effectively stiffens the distal portion of the coil, but also increases the outer diameter of the coil. Moreover, the change in outer diameter of the coil where the sleeve begins and ends results in a less than smooth outer surface which might hinder travel of the instrument through the narrow lumen of the endoscope and might cause additional wear to the endoscope.

SUMMARY OF THE INVENTION

It is therefore an object of the invention to provide a flexible microsurgical instrument having a flexible coil where the distal portion of the coil can be made stiff without increasing its outer diameter.

It is another object of the invention to provide a flexible microsurgical instrument having a flexible coil where the distal portion of the coil can be made stiff without compromising the smoothness of the outer surface of the coil.

In accord with these objects which will be discussed in detail below, the flexible microsurgical instrument according to the invention has a distal end effector, a proximal actuating assembly and a flexible coil connecting the two, with a distal portion of the flexible coil being ground to a smaller outer diameter than the remainder of the coil thereby reducing its thickness. A stiffening sleeve is provided over the ground distal portion of the coil. The sleeve has a thickness substantially equal to one half the difference in the diameters of the ground distal end of the coil and the remainder of the coil. Therefore, when the stiffening sleeve is provided, the outer diameter of the coil is not increased and the smooth outer surface of the coil is maintained.

Additional objects and advantages of the invention will become apparent to those skilled in the art upon reference to the detailed description taken in conjunction with the provided figures.

BRIEF DESCRIPTION OF THE DRAWINGS

FIG. 1 is a broken longitudinal cross sectional view of the proximal actuation handle of a flexible microsurgical instrument; and FIG. 2 is a broken longitudinal cross sectional view of the distal end of the flexible coil with a stiffening sleeve and a forceps end effector.

DETAILED DESCRIPTION OF THE PREFERRED EMBODIMENT

Referring generally to FIGS. 1 and 2, a flexible microsurgical instrument 10 is shown. The instrument 10 has a proximal actuation handle 12 and a flexible member or coil 14 coupling the handle 12 to a distal end effector 18. A pair of control wires 20, 22 extend through the coil 14 and are coupled at their proximal ends to a movable part 24 of the handle 12 and at their distal ends to the end effector 18.

As shown in FIG. 1, the proximal actuation handle 12 typically includes a stationary portion 26 having a distal throughbore 27, a central slot 28, a proximal thumb ring 30, and a displaceable spool 24 having a cross member 32 which is slidably disposed on the stationary portion 26 so that the cross member 32 passes through the slot 28. The proximal end of coil 14 is mounted in the distal throughbore 27 of the stationary part 26 of the handle 12 and the control wire 20, 22 extend through the throughbore 27 into the slot 28 where they are coupled to the cross member 32 of the spool 24 by a set screw 34. Those skilled in the art will appreciate that movement of the spool 24 relative to the stationary portion 26 effects a translational movement of the control wires relative to the coil.

According to the invention, about nine inches of the distal portion 36 of the coil 14 are ground to a reduced outer diameter and covered with a stiffening sleeve 38. The outer diameter of the coil 14 is typically approximately 0.082" (2.1 mm) and the ground portion has a reduced diameter of approximately 0.072" (1.8 mm). The stiffening sleeve 38 stiffens the distal portion 36 of the coil 10 without increasing its outer diameter. According to a presently preferred embodiment of the invention, the stiffening sleeve 38 is a TEFLON FEP shrink wrap tube which is approximately eight inches in length, has an inner diameter of approximately 0.072 inches, an outer diameter of approximately 0.082 inches and is approximately 0.005 inches thick. The thickness of the stiffening sleeve 38 is preferably substantially equal to one half the difference in the diameters of the ground distal portion 36 and the remainder of the coil 14 so as to provide a smooth outer surface for the coil and a substantially continuous outer diameter for the coil. In other words, the outer diameter of the sleeve 38 is substantially equal to the outer diameter of the coil 14.

The end effector 18 shown in FIG. 2 generally includes a pair of identical jaws 40, 42 and a clevis 44. Each jaw 40, 42 has a proximal tang 41, 43, a distal toothed cup 46, 48, and a transverse bore 50, 52. The proximal tang 41, 43 of each jaw 40, 42 is coupled to the distal end of a control wire 20, 22 which extends through the flexible coil 14. The proximal end of each control wire 20, 22 is coupled to the cross member 32 of the spool 24 (FIG. 1). The jaws 40, 42 are attached to the clevis 44 by a clevis pin 54 which passes through the transverse bore 50, 52 of each jaw 40, 42. The clevis 44 has a proximal hub 56 having an inner diameter substantially equal to the outer diameter of the ground distal portion 36 of the coil 14. The outer diameter of the hub 56 is substantially equal to the outer diameter of the remainder of the coil 14. Thus, the transition from the clevis hub 56 to the stiffening sleeve 38 to the remainder of the coil 14 is substantially smooth with a continuous relatively constant diameter. Operation of the forceps end effector is described in detail in U.S. Pat. No. 5,228,451 to Bales et al.

There has been described and illustrated herein a flexible microsurgical instrument having a distal portion which is ground to a reduced diameter and covered with a stiffening sleeve. While a preferred embodiment of the invention has been described, it is not intended that the invention be limited thereto, as it is intended that the invention be as broad in scope as the art will allow and that the specifications be read likewise. Thus, while the invention has been described with particular reference to endoscopic biopsy instruments having a coil, it will be appreciated that the inventive concepts disclosed herein can be advantageously applied to other types of surgical instruments as well with other types of hollow members. Moreover, while the stiffening sleeve has been disclosed as a TEFLON shrink wrap tube, it will be recognized that other materials can be used to achieve substantially the same result in substantially the same manner. Also, while the length of the distal portion of the flexible coil which is ground to a reduced diameter is typically eight or nine inches, it will be understood that the length may be varied according to the particular application for which the instrument is designed. Further, while the reduced diameter portion of the coil has been described as being ground to a reduced diameter, it will be appreciated that methods other than grinding can be used to provide the reduced diameter portion of the coil, although grinding is preferred. In addition, while the actuation handle has been shown as a stationary member having a thumb ring and a movable spool, it will be understood that different types of actuating handles can be used to achieve substantially the same result in substantially the same manner. It will therefore be appreciated by those skilled in the art that yet other modifications could be made to the provided invention without deviating from its spirit and scope as so claimed.

I claim:
1. A flexible microsurgical instrument, comprising:
   a) a proximal actuation handle;
   b) a flexible member having a proximal end and a distal end and a first outer diameter, said proximal end of said flexible member being coupled to said proximal actuation handle, and a distal portion of said flexible member having a second outer diameter which is smaller than said first outer diameter;
   c) at least one control wire having a proximal end and a distal end and extending through said flexible member, said proximal end of said at least one control wire being coupled to said proximal actuation handle such that manipulation of said proximal actuation handle causes a translational movement of said at least one control wire relative to said flexible member;
   d) a clevis coupled to said distal end of said flexible member, said clevis having a proximal hub surrounding part of said distal portion of said flexible member and having an outer diameter which is substantially equal to said first outer diameter;
   e) at least one end effector coupled to said clevis and to said distal end of said at least one control wire such that translational movement of said at least one control wire relative to said flexible member causes a movement of said end effector; and
   f) a stiffening sleeve covering said distal portion of said flexible member up to said proximal hub of said clevis, said stiffening sleeve having an outer diameter substantially equal to said first outer diameter.

2. A flexible microsurgical instrument according to claim 1, wherein:
   said distal portion of said flexible member is ground to provide said second diameter which is smaller than said first diameter.

3. A flexible microsurgical instrument according to claim 1, wherein:
   said stiffening sleeve has an inner diameter substantially equal to said second diameter.

4. A flexible microsurgical instrument according to claim 1, wherein:
   said at least one end effector includes a pair of biopsy forceps.

5. A flexible microsurgical instrument according to claim 1, wherein:
   said distal portion is approximately eight to nine inches long.

6. A flexible microsurgical instrument according to claim 1, wherein:
   said first outer diameter is approximately 0.082 inches and said second outer diameter is approximately 0.072 inches.

7. A flexible microsurgical instrument according to claim 1, wherein:

said stiffening sleeve is a TEFLON FEP shrink wrap tube.

8. A flexible microsurgical instrument according to claim 1, wherein:
said proximal actuation handle comprises a stationary portion coupled to said proximal end of said flexible member and a displaceable spool coupled to said proximal end of said at least one control wire.

9. A flexible microsurgical instrument according to claim 1, wherein:
said proximal hub of said clevis has an inner diameter substantially equal to said second outer diameter.

10. A flexible microsurgical instrument according to claim 1, wherein:
said flexible member is a coil.

11. A flexible microsurgical instrument, comprising:
a) a proximal actuation handle;
b) a flexible coil having a proximal end and a distal end and a first outer diameter, said proximal end of said flexible coil being coupled to said proximal actuation handle, and a ground distal portion of said flexible coil having a second outer diameter which is smaller than said first outer diameter;
c) at least one control wire having a proximal end and a distal end and extending through said flexible coil, said proximal end of said at least one control wire being coupled to said proximal actuation handle such that manipulation of said proximal actuation handle causes a translational movement of said at least one control wire relative to said flexible coil;
d) a clevis coupled to said distal end of said flexible coil, said clevis having a proximal hub surrounding part of said distal portion of said flexible coil and having an outer diameter which is substantially equal to said first outer diameter, and an inner diameter substantially equal to said second outer diameter;
e) at least one biopsy forceps end effector coupled to said clevis and to said distal end of said at least one control wire such that translational movement of said at least one biopsy forceps end effector relative to said flexible coil causes a movement of said one biopsy forceps end effector; and
f) a stiffening sleeve covering said distal portion of said flexible coil up to said proximal hub of said clevis, said stiffening sleeve having an outer diameter substantially equal to said first outer diameter, and an inner diameter substantially equal to said second diameter.

12. A flexible microsurgical instrument according to claim 11, wherein:
said distal portion is approximately eight to nine inches long,
said first outer diameter is approximately 0.082 inches and said second outer diameter is approximately 0.072 inches.

13. A flexible microsurgical instrument according to claim 11, wherein:
said stiffening sleeve is a TEFLON FEP shrink wrap tube.

14. A flexible microsurgical instrument according to claim 11, wherein:
said proximal actuation handle comprises a stationary portion coupled to said proximal end of said flexible coil and a displaceable spool coupled to said proximal end of said at least one control wire.

* * * * *